United States Patent [19]

Inoue et al.

[11] Patent Number: 4,968,495
[45] Date of Patent: Nov. 6, 1990

[54] CHEMICALLY MODIFIED BILIRUBIN OXIDASE

[75] Inventors: Masayasu Inoue; Hiroshi Maeda, both of Kumamoto, Japan

[73] Assignee: Amano Pharmaceutical Co., Ltd., Aichi, Japan

[21] Appl. No.: 226,088

[22] Filed: Jul. 29, 1988

[30] Foreign Application Priority Data

Aug. 28, 1987 [JP] Japan ................................ 62-215570

[51] Int. Cl.$^5$ .................... A61K 37/50; C12N 11/02; C12N 11/10; C12N 9/02
[52] U.S. Cl. .................................. 424/94.4; 424/94.3; 424/10; 435/174; 435/177; 435/178; 435/179; 435/188; 435/189
[58] Field of Search .................. 424/94.3, 94.4, 10; 435/174, 177-179, 188, 189; 436/97

[56] References Cited

U.S. PATENT DOCUMENTS

| | | | |
|---|---|---|---|
| 2,066,105 | 12/1936 | Hagedorn et al. | 424/94.3 |
| 4,004,979 | 1/1977 | Avrameas et al. | 424/94.3 |
| 4,179,337 | 12/1979 | Davis et al. | 424/94.3 |

OTHER PUBLICATIONS

Lavin et al, Science, (Nov. 1985), vol. 230, No. 4725, pp. 543-545.

*Primary Examiner*—Jacqueline Stone
*Attorney, Agent, or Firm*—Wenderoth, Lind & Ponack

[57] ABSTRACT

A bilirubin oxidase derivative resulting from chemical modification of a water-soluble polymeric substance. The chemically modified bilirubin oxidase is useful as a drug for treating jaundice.

10 Claims, 3 Drawing Sheets

CHEMICALLY MODIFIED BILIRUBIN OXIDASE

BACKGROUND OF THE INVENTION

This invention relates to a chemically modified bilirubin oxidase, and more specifically, to a bilirubin oxidase derivative resulting from chemical modification of bilirubin oxidase with a water-soluble polymeric substance.

The chemically modified bilirubin oxidase provided by this invention is useful as a drug for treating jaundice because it acts to specifically decompose and remove bilirubin which abnormally increases in blood in jaundice, and has very high stability in blood.

Jaundice is a condition in which bilirubin in blood increases abnormally to yellow the skin, mucous membranes and other tissues. Jaundice accompanying various hepatic diseases involves strong cytotoxin of bilirubin, and often brings about serious results (see Maisels, M. J.: Neonatology, edited by Avery, G. B., Lippicott Co., Philadelphia, 1981, pages 473–544). Thus, neonatal jaundice is treated by light therapy or therapy by exchange transfusion (see Cohen, A. V. and Ostrow, J. D.: Pediatrics, 65: 740–750, 1980). Extracorporeal therapies have also been attempted. For example, bilirubin in blood is adsorbed on various resins (see Scharschmidt, B. F. et al.: J. Clin. Invest., 53: 786–795, 1974), or decomposed and removed by using bilirubin oxidase fixed to a carrier such as a polysaccharide (e.g., cellulose, dextran or agarose), polyacrylamide gel, porous glass and polystyrene (see Labin, A. et al.: Science, 230: 543–545, 1985).

The above therapeutic methods have some difficulties such as a low therapeutic efficiency, securing of transfusion preparations, the non-specificity of adsorbing components and the complexity of operation.

To remove bilirubin in blood from jaundice patients, the use of bilirubin oxidase is excellent in view of its reaction specificity. So far, the in vivo administration of the bilirubin oxidase has been impossible because of its extremely poor stability in vivo and its antigenicity.

SUMMARY OF THE INVENTION

It is an object of this invention to provide a chemically modified bilirubin oxidase which specifically decomposes and removes bilirubin in blood and has a very long half-life in blood.

According to this invention, the above object is achieved by providing a bilirubin oxidase derivative chemically modified with a water-soluble polymeric substance (to be referred to as the "bilirubin oxidase derivative").

The term "chemically modified", as used in the present specification and claims, means that the water-soluble polymeric substance is bonded to bilirubin oxidase by a covalent bond.

DETAILED DESCRIPTION OF THE PREFERRED EMBODIMENTS

Drawings

WATER-SOLUBLE POLYMERIC SUBSTANCE

Examples of the water-soluble polymeric substance used to modify bilirubin oxidase include polyalkylene glycols such as polyethylene glycol, polypropylene glycol and ethylene oxide/propylene oxide copolymer; polyvinyl alcohol; polysaccharides such as dextran, pullulan and inulin; a partially hydrolyzed copolymer of styrene and maleic anhydride; a partially half-esterified copolymer of styrene and maleic anhydride (e.g., the methyl, ethyl, propyl, n-butyl, methoxyethyl, ethoxyethyl, 1,3-dimethoxy-2-propyl, 2,3-dimethoxy-1-propyl, 1,3-diethoxy-2-propyl or 2-ethoxy-3-methoxy-1propyl ester); a partially hydrolyzed copolymer of divinyl ether and maleic anhydride; a partially half-esterified copolymer of divinyl ether and maleic anhydride (e.g., the methyl, ethyl, propyl, n-butyl, methoxyethyl, ethoxyethyl, 1,3-dimethoxy-2-propyl, 2,3-dimethoxy-1-propyl, 1,3-diethoxy-2-propyl or 2-ethoxy-3-methoxy-1-propyl ester); a partially hydrolyzed copolymer of acrylic acid and maleic anhydride; a partially half-esterified copolymer of acrylic acid and maleic anhydride (e.g., the methyl, ethyl, propyl, n-butyl, methoxyethyl, ethoxyethyl, 1,3-dimethoxy-2-propyl, 2,3-dimethoxy-1-propyl, 1,3-diethoxy-2-propyl or 2-ethoxy-3-methoxy-1-propyl ester); Ficoll; polyamino acids such as polyglutamic acid, polyaspartic acid and polylysine; and albumin.

Of these water-soluble polymeric substances, the polyalkylene glycols, polysaccharides and the partially hydrolyzed or partially half-esterified copolymer of styrene and maleic anhydride are preferably used as chemical modifiers for bilirubin oxidase.

Preferred bilirubin oxidase derivatives obtained by chemical modification include products of chemical modification of bilirubin oxidase with polyalkylene glycol, products of chemical modification of bilirubin oxidase with polysaccharides and products of chemical modification of bilirubin oxidase with a partially hydrolyzed or partially half-esterified copolymer of styrene and maleic anhydride. These preferred bilirubin oxidase derivatives will be described more specifically hereinafter.

[A] The products of chemical modification of bilirubin oxidase with polyalkylene glycols ("bilirubin oxidase derivatives (I)") include compounds represented by general formula (I).

wherein

[BOase] represents (a) a bilirubin oxidase containing 1 to 10 amino acid units (x) resulting from removing 1 or 2 hydrogen atoms from amino acid units having a nucleophilic moiety which exist in the bilirubin oxidase molecule or (b) a bilirubin oxidase residue containing to 98 amino acid units (y) resulting from removing OH from the carboxyl groups of amino acid units which exist in the bilirubin oxidase molecule;

l and m are 0 when [BOase] represents the bilirubin oxidase residue (a), and when [BOase] represents the bilirubin oxidase residue (b), m is at least 1 and the sum of m+l is an integer equal to the number of the amino acid units (y) in the residue (b), which is preferably 1 to 30, more preferably 5 to 15;

$R^1$ and $R^2$ each represent a hydrogen atom or a lower alkyl group such as a methyl or ethyl group;

$R^3$ represents a hydrogen atom, a lower alkyl group such as a methyl or ethyl group, or a bond to $(Z^1)$;

A represents a divalent hydrocarbon group which may have a nitrogen, oxygen or sulfur atom;

$(Z^1)$ represents a group derived from a monoalkoxypolyalkylene glycol; and when [BOase] represents the bilirubin oxidase residue (a), n represents an integer equal to the number of the amino acid units (x) contained in the residue (a), and when [BOase] represents the bilirubin oxidase residue (b), n represents an integer equal to the number of the amino acid units (y) in the residue (b), which is preferably 1 to 30, more preferably 5 to 15.

The divalent hydrocarbon group for A which may have a nitrogen, oxygen or sulfur atom may include, for example, where p represents an integer of of 1 to 10, preferably 4 to 6, The group derived from a monoalkoxypolyalkylene glycol, which is represented by $(Z^1)$, includes polyalkylene glycols having such a structure that one end hydroxyl group is substituted by an alkoxy group such as a methoxy, ethoxy or propoxy group, and the other end has the grouping $$-\overset{O}{\underset{\|}{C}}-(\text{PAG-b}),\ =CH-(\text{PAG-b})\ \text{or}\ -CH_2-(\text{PAG-b}).$$

In the above formulae, (PAG-a) represents a residue resulting from removing the hydroxyl group from the terminals of a monoalkoxypolyalkylene glycol; (PAG-b) represents a residue resulting from removal of the hydroxymethyl group from the terminals of a monoalkoxypolyalkylene glycol; and $R^4$ represents a chlorine atom or a hydroxyl group.

Examples of the polyalkylene glycols are polyethylene glycol, polypropylene glycol and a copolymer of ethylene oxide and propylene oxide which have an average molecular weight of generally 400 to 30,000, preferably 1,000 to 20,000.

The term "lower", as used in the present specification and the appended claims to qualify a group or a compound, means that the group or compound so qualified has not more than 6, preferably not more than 4, carbon atoms.

The bilirubin oxidase derivative (I) may be produced, for example, by (i) reacting bilirubin oxidase with a monoalkoxypolyalkylene glycol with activated ends; or (ii) chemically modifying bilirubin oxidase with a diamine compound and reacting the chemically modified product with a monoalkoxypolyalkylene glycol with activated ends, and as required, reducing the resulting bilirubin oxidase derivative.

The chemical modification of bilirubin oxidase with the diamine compound (the product will be referred to as the diamine-modification product) can be carried out usually by reacting bilirubin oxidase with such a diamine compound as 1,4-diaminobutane, 1,6-diaminohexane, 1,8-diaminooctane, 1,4-diaminobenzene, p-xylenediamine, N,N-bis(3-aminopropyl)methylamine, bis(aminomethyl)ether, bis(3-aminopropyl)ether, ethylene glycol bis(3-aminopropyl)ether, 4,4'-diaminodiphenyl ether and 4,4'-thiodianiline in a buffer such as a borate buffer or a phosphate buffer in the presence of a dehydrating agent such as 1-ethyl-3-(3-dimethylaminopropyl)carbodiimide or N-ethoxycarbonyl-2-ethoxy-1,2-dihydroquinoline at a temperature of about 0° C. to about 40° C. for about 1 to 30 hour. After the reaction, the reaction mixture is subjected to a usual separating means such as gel filtration or ultrafiltration, and the resulting diaminemodification product is separated. The separated diaminemodification product is used in the reaction with the monoalkoxypolyalkylene glycol with activated ends.

The reaction of bilirubin oxidase or its diamine-modification product with the monoalkoxypolyalkylene glycol having activated ends will be described below.

For example, the following three types of compounds may be used as the terminally activated monoalkoxypolyalkylene glycol. (PAG-a) and (PAG-b) in the following formulae have the same definitions as given above.

(1) Cyanuric Chloride Type (2) Imide Ester Type (3) Aldehyde Type (1) When a cyanuric chloride-type monoalkoxypolyalkylene glycol is used as the starting material:

The reaction of bilirubin oxidase or its diamine-modification product with the cyanuric chloridetype monoalkoxypolyalkylene glycol is carried out, for example, in a borate buffer at a pH of 8 to 10 and a temperature of about 0° C. to about 40° C. for about 1 to 30 hours. The reaction mixture is subjected to, for example, gel filtration or ultrafiltration to remove the unreacted cyanuric chloride-type monoalkoxypolyalkylene glycol and thus to obtain the bilirubin oxidase derivative (I).

(2) When the imide ester-type monoalkoxypolyalkylene glycol is used as the starting material:

The reaction of bilirubin oxidase or its diamine-modification product with the imide ester-type monoalkoxypolyalkylene glycol is carried out, for example, in a phosphate buffer under weak basicity at a temperature of about 0° C. to about 40° C. for several minutes to several hours. The reaction mixture is subjected to, for example, ultrafiltration to remove the unreacted imide ester-type monoalkoxypolyalkylene glycol or its decomposition product and to obtain the bilirubin oxidase derivative (I).

(3) When the aldehyde-type monoalkoxypolyalkylene glycol is used as the starting material:

The reaction of bilirubin oxidase or its diamine-modification product with the aldehyde-type monoalkoxypolyalkylene glycol is usually carried out in the presence or absence of a boron-containing reducing agent such as sodium borohydride or sodium cyanoborohydride The amount of the aldehyde-type monoalkoxypolyalkylene glycol used is generally 1 to about 10,000 moles per mole of the bilirubin oxidase or its diamine-modification product. By adjusting the amounts of the bilirubin oxidase or its diamine-modification product and the aldehyde-type monoalkoxypolyalkylene glycol within this range, the degree of chemical modification with the monoalkoxypolyalkylene glycol in the bilirubin oxidase derivative (I) can be varied. The boron-containing reducing agent is used ordinarily in an amount of 1 to about 100 moles per mole of the aldehyde-type monoalkoxypolyalkylene glycol. The reaction solvent may preferably be a buffer such as a phosphate or borate buffer. An organic solvent, which does not deactivate the enzyme activity of bilirubin oxidase nor impair the reaction, for example a lower alkanol such as methanol, ethanol or isopropanol, acetonitrile or dimethyl sulfoxide, may be used in the reaction system. The pH of the reaction system is adjusted to 8 to 11. The reaction is carried out at a temperature which does not degenerate bilirubin oxidase, for example at about 0° C. to about 80° C., preferably about 0° C. to about 50° C. After the reaction, the reaction mixture is subjected to, for example, gel filtration or ultrafiltration to remove the unreacted aldehyde-type monoalkoxypolyalkylene glycol and to obtain the bilirubin oxidase derivative (I).

Typical examples of the monoalkoxypolyalkylene glycol used in the above methods include monoalkoxypolyethylene glycol, monoalkoxypolypropylene glycol and monoalkoxy/ethylene oxide/propylene oxide copolymer. The monoalkoxypolyethylene glycol is preferred, and monomethoxypolyethylene glycol is especially preferred. The starting polyethylene glycol may have an average molecular weight of 400 to 30,000. Especially good bilirubin oxidase derivative (I) can be obtained when polyethylene glycol having an average molecular weight of 1,000 to 20,000 is used.

[B] The bilirubin ox idase derivative ("bilirubin oxidase derivative (II)") obtained by chemical modification with polysaccharides is typically represented by the following general formula (II).

wherein [BOase], $R^1$, $R^2$, $R^3$, A, l, m and n are as defined with regard to general formula (I); and $Z^2$ represents a group derived from a polysaccharide.

The group $Z^2$ derived from the polysaccharide may have any of the following structures as a bonding site.

In the above formulae, (Psac-a) represents a polysaccharide residue resulting from removing the formyl groups from an aldehyde-type polysaccharide obtained by partially oxidizing the constituent monosaccharides of the polysaccharide, and (Psac-b) represents a polysaccharide residue resulting from removing the hydroxyl groups from the constituent monosaccharides from the polysaccharide. The bilirubin oxidase derivative (II) can be produced, for example, by reacting bilirubin oxidase or its diamine-modification product with an activated polysaccharide and if required, reducing the resulting bilirubin oxidase derivative (II).

Examples of the activated polysaccharide are (1) aldehyde-type polysaccharides (Psac-a)-CHO obtained by partially oxidizing the constituent monosaccharides of polysaccharides in a customary manne with oxidizing agents such as sodium periodate and potassium periodate; and (2) polysaccharides, such as (Psac-b)-O-CN, obtained by partially activating polysaccharides with cyanogen bromide in a customary manner. (Psac-a) and (Psac-b) are as defined above.

(1) When the aldehyde-type polysaccharide is used as the starting material:

The bilirubin oxidase derivative (II) is produced from bilirubin oxidase or its diamine-modification product by, for example, the same method as used in the produc- tion of the bilirubin oxidase derivative (I) from bilirubin oxidase or its diamine-modification product and the aldehyde-type monoalkoxypolyalkyleneglycol. This method gives the bilirubin oxidase derivative (II) [the structure of the bonding site: —N=CH—(Psac-a)] and the corresponding reduced bilirubin oxidase derivative (II) the structure of the binding site: —NH—CH$_2$—(P-sac-a)].

(2) When the cyanogen bromide-activated polysaccharide is used as the starting material:

The reaction of bilirubin oxidase or its diamine-modification product with the cyanogen bromide-activated polysaccharide is carried out, for example, in a weakly basic aqueous solution at room temperature for several hours to about 1 day. The reaction product is, for example, subjected to gel filtration to remove the unreacted cyanogen bromide-activated polysaccharide to obtain bilirubin oxidase derivative (II).

Examples of the starting polysaccharide are dextran, pullulan and inulin. Usually, dextran is preferred. The dextran that can be used has an average molecular weight of generally 2,000 to 200,000. When dextran having an average molecular weight of 5,000 to 70,000 is used, the resulting bilirubin oxidase derivative (II) is especially good.

[C] As bilirubin oxidase derivative [to be referred to as the "bilirubin oxidase derivative (III)"] obtained by chemically modifying bilirubin oxidase with the partially hydrolyzed or partially half-esterified copolymer of styrene and maleic acid can be represented by the following general formula (III)

(III)

wherein [BOase], R$^1$, R$^2$, R$^3$, A, l, m and n are as defined above; and Z$^3$ represents a monovalent group derived from a copolymer having an average molecular weight of 800 to 20,000 and composed of
  (a) a group of the formula

(b) a group of the formula wherein R$^5$ represents a hydrogen atom, or a group resulting from removal of the hydroxyl groups from an alkanol having 1 to 4 carbon atoms, an ethylene glycol monoalkyl ether containing an alkyl moiety having 1 or 2 carbon atoms or a glycerin dialkyl ether containing an alkyl moiety having 1 or 2 carbon atoms, and
  (c) a group of the formula wherein the bond from the carbon, atom of the carbonyl group is bonded to as structural units.

The bilirubin oxidase derivative (III) can be produced by, for example, reacting bilirubin oxidase or its diamine modification product with a specific copolymer having an average molecular weight of 800 to 20,000 and composed of
  (a) a group of the formula (b) a group of the formula wherein R$^5$ is as defined, and
  (c) a group of the formula as structural units (this copolymer will be referred to simply as the copolymer).

The reaction of bilirubin oxidase or its diamine-modification product with the copolymer is carried out usually by dissolving bilirubin oxidase or its diamine-modification product in an aqueous solution of a salt such as sodium carbonate, sodium bicarbonate, sodium acetate or sodium phosphate, and adding the powdery copolymer or a solution of the copolymer in an organic solvent such as dimethyl sulfoxide to the resulting solution. During the reaction, the solution should be maintained at a pH of 8 to 11. If the pH of the solution is lower than 8, the solubility of the copolymer is lowered, and the reaction does not proceed. If, on the other hand, its pH is higher than 11, the enzyme activity of bilirubin oxidase is destroyed so that it is impossible to obtain an effective bilirubin oxidase derivative (III). The reaction temperature is usually about 3 to 50° C., preferably 3° to 40° C.. The reaction time, which varies with the reaction temperature and the method of adding the copolymer, is usually 10 minutes to 3 hours. The amount of the copolymer may be in the range of about 0.5 to 100 moles per mole of bilirubin oxidase or its diamine-modification product. The number of molecules of the copolymer to be bonded to bilirubin oxidase or its diamine-modification product may be adjusted by the amount of the copolymer.

The resulting reaction mixture contains the bilirubin oxidase derivative (III). the unreacted bilirubin oxidase or its diamine-modification product, the copolymer, etc. The bilirubin oxidase derivative (III) as a solid can be obtained by, for example, filtering the reaction mixture, subjecting the filtrate to gel filtration, as required, subjecting the eluate containing the resulting bilirubin oxidase derivative (III) to hydrophobic chromatography and then to ultrafiltration to concentrate it, and then lyophilizing it.

As a result of the above reaction, the nucleophilic part of bilirubin oxidase or its diamine-modification product or the introduced amino groups is bonded to the maleic anhydride ring of the copolymer to give the bilirubin oxidase derivative (III).

The starting copolymer usually contains 0.5 to 2 maleic anhydride ring is per molecule on an average. When one maleic anhydride ring is bonded to the nucleophilic part of bilirubin oxidase or its diamine-modification product or the introduced amino groups, the remaining maleic anhydride rings rarely react with other amino groups, but tend to react with water to become ring-opened and change to a group of the formula derived from maleic acid. Accordingly, the structural unit of the bilirubin oxidase derivative (III) also contains the group (b) in which $R^5$ is a hydrogen atom.

When the partially half-esterified copolymer is used as the starting material, the structural unit of the resulting bilirubin oxidase derivative (III) contains not only the half-esterified product of the above group derived from maleic acid but also a small amount of the group derived from maleic acid as the groups (b). There is a possibility of formation as a by-product of a compound resulting from reaction of one molecule of the copolymer with a plurality of molecules of bilirubin oxidase or its diamine-modification product to induce bonding of the maleic anhydride rings of the copolymer to the nucleophilic portion of bilirubin oxidase or its diamine modification product or the introduced amino groups. It should be understood however that the bilirubin oxidase derivative (III) containing a small amount of the by-product is also included within the scope of the invention. However, in view of the fact that an active compound of a drug preferably has a single chemical structure, the bilirubin oxidase derivative (III) containing a large amount of the by-product is preferably used after the by-product is removed by a separating operation such as gel filtration.

The bilirubin oxidase derivative (III) obtained by the above reaction is a mixture of products obtained as a result of bonding of copolymers having various numbers of molecules to bilirubin oxidase or its diamine-modification product, and the numbers of molecules of the copolymers bonded to the bilirubin oxidase or its diamine-modification product in the individual bilirubin oxidase derivatives (III) are not the same. Accordingly, in the above formula representing the bilirubin oxidase derivative (III), n represents the average number of the molecules of the copolymer bonded to one molecule of bilirubin oxidase or its diamine-modification product. But when it is desired to obtain the bilirubin oxidase derivative (III) in which the numbers of molecules of the copolymer bonded to bilirubin oxidase or its diamine-modification product are the same, the bilirubin oxidase derivative (III) obtained by the above method may be subjected to a separating operation such as gel filtration to give the desired bilirubin oxidase derivative (III).

There is a possibility that in the above reaction and the treatment after the reaction, the carboxyl groups of the bilirubin oxidase derivative (III) will form an alkali metal salt or an ammonium salt. It should be understood that bilirubin oxidase derivatives (III) having carboxyl groups forming these salts are within the scope of the invention.

The starting copolymer may be obtained, for example, by partially hydrolyzing a copolymer of maleic anhydride and a monomer corresponding to the structural unit (a) shown above [a small amount (0.5 to 2 on an average per molecule) of maleic anhydride rings remain and the other maleic anhydride rings are hydrolyzed], or partially half-esterifying a copolymer of maleic anhydride hydride and a monomer corresponding to the structural unit (a) with an alcohol [a small amount (0.5 to 2 on an average per molecule) of maleic anhydride rings remain, and the other maleic anhydride rings are half-esterified]. Examples of the resulting copolymer include a partially hydrolyzed copolymer of styrene and maleic anhydride, and half-esterified copolymers (for example, methyl, ethyl, propyl, n-butyl, methoxyethyl, ethoxyethyl, 1,3-dimethoxy2-propyl, 2,3-dimethoxy-1-propyl, 1,3-diethoxy-2-propyl, and 2-ethoxy-3-methoxy-1-propyl esters) of styrene and maleic anhydride.

These copolymers have both hydrophobic and hydrophilic groups and therefore moderate hydrophobicity. They also have carboxyl groups having high polarity. Accordingly, the bilirubin oxidase derivative (III) having such a copolymer bonded has the reversible bindability to a serum protein and a biological membrane. Hence, its half life in blood is prolonged and its migrability to an organ is improved. A bilirubin oxidase derivative (III) having a group derived from styrene as the constituent unit (a) and a half-esterified group as the constituent unit (b) has higher hydrophobicity and is preferred for the exhibition of these effects.

In the copolymer, the mole ratio of the constituent element (a) to the constituent elements (b) and (c) is preferably substantially within the range of about 1 to 1.3, and advantageously, it is usually about 1. If this mole ratio is less than 1, it is difficult to obtain a copolymer of maleic anhydride and a monomer corresponding to the structural unit (a). If the mole ratio is higher than 1.3 and the constituent unit (b) is half-esterified, the copolymer has poor solubility in an aqueous solution of a salt when it is dissolved in the aqueous solution and reacted with bilirubin oxidase or its diamine-modification product.

The above copolymers are all known, and may have a weight average molecular weight of usually 800 to 20,000. From the standpoint of migration of the bilirubin oxidase derivative (III) to a lesion, the weight average molecular weights of the copolymers are preferably 800 to 8,000. There is no particular restriction on the molecular weight distribution of the copolymer. A product obtained by partially hydrolyzing or partially half-esterifying copolymer obtained by radical copolymerizing maleic anhydride and a monomer corresponding to the constituent unit (a) (a weight average molecular weight ($\overline{M}w$)/number average molecular weight ($\overline{M}n$) ratio of about 2.0 or higher) without frictionation may be used as the starting material. Alternatively, it is possible to fractionate the copolymer to narrow its molecular weight distribution, partially hydrolyzing or partially half-esterifying it, and using the product as the starting material.

BILIRUBIN OXIDASE

The enzyme bilirubin oxidase used in this invention may be of any origin. For example, bilirubin oxidase derived from microorganisms of the genus Myrothecium or Coprinus may be used. Examples of the microorganisms of the genus Myrothecium capable of producing bilirubin oxidase *Myr. verrucaria* MT-1, FERM-BP 653 (Agricultural and Biological Chemistry, vol. 45, 2383-2384, 1981), *Myr. verrucaria* IFO 6113, *Myr. verrucaria* IFO 6133, *Myr. verrucaria* IFO 6351, *Myr. verrucaria* IFO 9056, *Myr. cinctum* IFO 9950, and *Myr. roridum* IFO 9531 [Murao, S. and Tanaka, N.: Agric. Biol., Chem. 46: 2031-2037, 1982). Example of the microorganisms of the genus Coprinus capable of producing bilirubin oxidase are *Coprinus Cinereus* IFO 8371 and *Coprinus lagopides* IFO 30120 (see, for example, U.S. Pat. No. 4,554,249. These microorganisms may be subjected to liquid culture or solid culture by a conventional method. A purified product of bilirubin oxidase can be obtained by subjecting the culture broth to a usually operation such as extraction, salting out, dialysis, ion exchange and gel filtration [see, for example, Tanaka, N. and Murao, S.: Agric. Biol. Chem., 46 (10), 2499-2503, 1982].

The bilirubin oxidase so obtained acts on bilirubin and changes it to a nearly colorless product via biliverdin. As a result, the specific absorption (about 460 nm) of bilirubin decreases and its reducibility is lost. This enzyme is characterized by not producing hydrogen peroxide. Bilirubin oxidase has a molecular weight of about 52,000 to about 83,000 although it differs depending upon the origin.

UTILITY

As can be seen from the bilirubin oxidase derivative provided by this invention has a very long half life in blood and markedly reduces the bilirubin level in the blood as demonstrated by the results of Test Examples given hereinafter. Bilirubin oxidase derivatives obtained by chemical modification with polyethylene glycol have particularly good stability in blood and it activity of reducing the bilirubin level in blood in jaundice.

Furthermore, it has been determined that the bilirubin oxidase derivatives provided by this invention have little antigenicity and low toxicity in a toxicity test.

For the foregoing reasons, the bilirubin oxidase derivatives of the invention are effective as drugs for treating jaundice such as constitutional hyperbilirubinemia and neonatal jaundice. They are also useful as drugs for treating and preventing liver cirrhosis and hepatitis, particularly fulminant heptatitis.

The dose of the bilirubin oxidase derivative to be administered varies depending upon the type of the disease, the severity of the patient, and the patient's tolerance to the drug, but is usually 0.1 to 1000 mg, preferably 0.5 to 50 mg, per day per adult. The dose may be administered once or two or more divided portions a day. The drug may be administered by ordinary oral or parenteral routes such as oral, subcutaneous, intramuscular, intravenous, and intrarectal routes. In administration, the drug may be in any desired form suitable for a particular administration route.

The bilirubin oxidase derivative may be formulated for administration by using any conventional drug formulation method. A pharmaceutical composition comprising at least one bilirubin oxidase derivative may be prepared by a conventional galenical method using a pharmaceutically acceptable diluent or carrier and pharmaceutically acceptable adjuvants such as excipients.

For oral administration, the composition may desirably be provided in a form suitable for absorption from the digestive tract. Tablets and capsules for oral administration may be in a unit dosage form, and may contain conventional excipients, for example binders such as syrup, gum arabic, gelatin, sorbitol, tragacanth gum and polyvinyl pyrrolidone; molding agents such as lactose, cornstarch, calcium phosphate, sorbitol and glycine; lubricants such as magnesium stearate, talc, polyethylene glycol and silica; disintegrants such as potato starch; and acceptable wetting agents such as sodium laurylsulfate. The tablets may be coated by a method known in the art. Liquid preparations for oral administration may be in the form of, for example, an aqueous or oily suspension, a solution, a syrup or an elixir, or may be a dry product which is to be redissolved in a suitable vehicle such as water prior to use. These liquid preparations may contain normally used adjuvants, for example a suspending agent such as sorbitol syrup, methyl cellulose, glucose/sugar syrup, gelatin, hydroxyethyl cellulose, carboxymethyl cellulose, aluminum stearate gel or hydrogenated edible fats; an emulsifier such as lecithin, sorbitan monooleate or gum arabic; a non-aqueous vehicle such as almond oil, fractionated coconut oil, oily ester, propylene glycol and ethanol; and an antiseptic such as methyl p-hydroxybenzoate, propyl p-hydroxybenzoate or sorbic acid.

In preparing an injectable solution or a drip, the bilirubin oxidase derivative is dissolved in a solvent such as physiological saline or an injectable glucose solution, adjusting the concentration of the bilirubin oxidase to 2 to 20 mg/2 to 10 ml of solvent, and preparing the solution as a subcutaneous, intramuscular or intravenous injectable preparation in a customary manner. As required, a pH adjusting agent, a buffer, a stabilizer, a preservative, a solubilizing agent, etc. may be added to the aqueous solution during formulation.

The pharmaceutical composition may contain the bilirubin oxidase derivative in a concentration of generally about 0.01 to 50% by weight, preferably about 0.1 to 20% by weight, depending upon its form, etc.

The following Examples and Test Examples specifically illustrate the present invention.

EXAMPLE 1

Production of a Bilirubin Oxidase Derative by Chemical Modification with Polyethylene Glycol 200 mg of 2,4-bis(O-methoxypolyethylene glycol)-6-chloro-s-triazine (Seikagaku Kogyo Co., Ltd.; average molecular weight $\overline{M}w$ 20,000) was added to 1 ml of 0.2M phosphate buffer (pH 9.0) containing 5.2 mg of bilirubin oxidase (Sigma Co., molecular weight 52,000), and the mixture was incubated at 37° C. for 2 hours and then at 4° C. for 16 hours. The resulting mixture was charged onto a column (2×80 cm) filled with Sephadex ® G-100 (Pharmacia Co.) and gel-filtered. Phosphate buffer (pH 7.4) was used as an eluent, and the eluate was detected at 280 nm, and the eluate corresponding to the absorption part free from the unreacted 2,4-bis(O-methoxypolyethylene glycol)-6-chloro-s-triazine was separated. The solution containing the bilirubin oxidase derivative was lyophilized to give about 9 mg (about 4 mg as protein) of a powder. The recovered yield of the bilirubin oxidase derivative was 90% (the total recovery rate from the start).

Figure 1:
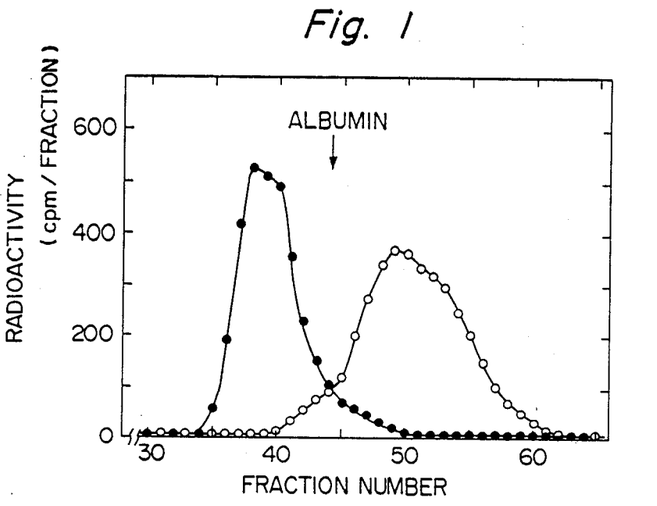
FIG. 1 shows gel chromatograms of the bilirubin oxidase derivative obtained in Example 1 and the bilirubin oxidase used.
Figure 2:
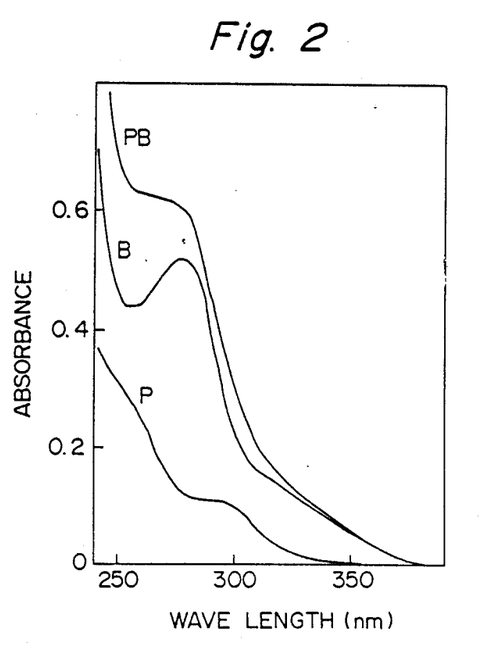
FIG. 2 shows the UV spectra of the bilirubin oxidase derivative obtained in Example 1, bilirubin oxidase used, and 2,4-bis(0-methoxypolyethylene glycol)-6-chloro-s-triazine.

The resulting bilirubin oxidase derivative was charged onto a column (1.6×40 cm) filled with Sephadex® G-150 (Pharmacia Co.) and fractionated by gel filtration. The bilirubin oxidase derivative was recovered in a fraction having a molecular weight of about 110,000. This molecular weight is about 60,000 higher than that of the non-treated bilirubin oxidase. From this, it was determined that the bilirubin oxidase derivative is a sample in which 6 molecules of monomethoxypolyethylene glycol was bonded to 1 molecule of bilirubin oxidase. Gel chromatograms of the bilirubin oxidase derivative and the non-treated bilirubin oxidase both labelled with $^{125}I$ are shown in FIG. 1. In the drawing, the closed circles show the gel chromatogram of the bilirubin oxidase derivative, and the open circles show the gel chromatogram of the non-treated bilirubin oxidase.

Figure 3:
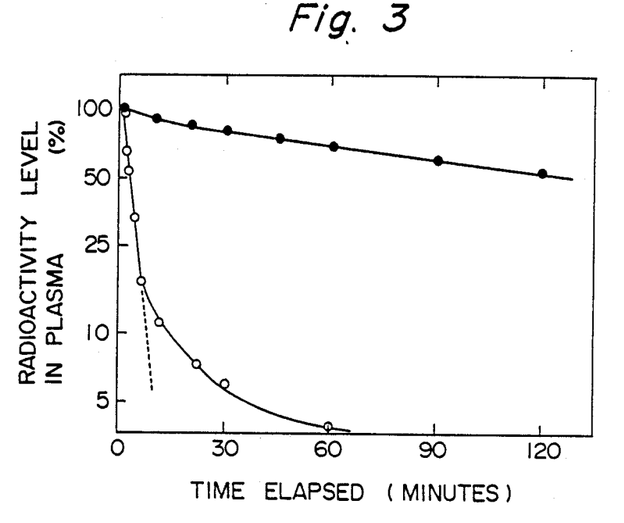
FIG. 3 is a graphic representation showing the concentrations of the bilirubin oxidase derivative obtained in Example 1 and the used bilirubin oxidase in blood which were measured with time in Test Example 1 and plotted in semilogarithm.

UV spectra of the bilirubin oxidase derivative, the non-treated bilirubin oxidase and the 2,4-bis(O-methoxypolyethylene glycol)-6-chloro-s-triazine were measured by using 20 mM phosphate buffer (pH 7.4) containing 0.15M sodium chloride. FIG. 3 shows the UV spectra as PB, B and P, respectively.

EXAMPLE 2

Production of a Bilirubin Oxidase Derivative by Chemical Modification with Polyethylene Glycol Six hundred milligrams of bilirubin oxidase (Amano Pharmaceutical Co., Ltd.) was dissolved in 80 ml of 0.01M phosphate buffer (pH 8.0), and then 1.86 g of 1,4-diaminobutane was added and completely dissolved. To the resulting solution was added 2.20 g of 1-ethyl-3-(3-dimethylaminopropyl)carbodiimide, and the mixture was left to stand overnight at 4° C. with stirring. The reaction mixture was charged onto a column (capacity 600 ml) filled with Sephadex® G-25 (Pharmacia Co.) equilibrated with 0.01M phosphate buffer, and fractions which were eluted at the exclusion limit were separated. The recovered yield of the reaction product up to this time was about 35%. When the reaction product was electrophoresed on a polyacrylamide gel (gel concentration 7.5%; pH 8.9), it was found that the bilirubin oxidase having 1,4-diaminobutane bonded thereto had an isoelectric point shifted to the basic side with respect to the non-treated bilirubin oxidase.

The resulting reaction product (in an amount corresponding to 25 mg as a bilirubin oxidase) was dissolved in 25 mg of 0.02M borate buffer (pH 10.0), and then 800 mg of monomethoxypolyethylene glycol activated with cyanuric acid (a product of Poly-Science Co., Ltd.; the average molecular weight $\overline{M}w$ of polyethylene glycol 5,000) was added and completely dissolved. The solution was incubated overnight at 4° C. The resulting reaction mixture as passed through a mini-module for ultrafiltration with a fractionation molecular weight of 13,000, and excess of the starting material derived from polyethylene glycol was removed, and the solution containing the bilirubin oxidase derivative was lyophilized. The enzyme activity of this derivative was 5 units/mg. The recovered yield of the bilirubin oxidase derivative was about 29% based on the non-treated bilirubin oxidase. The bilirubin oxidase derivative so obtained was electrophoresed on sodium dodecylsulfate/polyacrylamide gels (gel concentration 10%; pH 8.9). No band ascribable to bilirubin oxidase was observed, and a broad smeared band was detected on a higher molecular weight side than a position at which the band of bilirubin oxidase was to be observed.

EXAMPLE 3

Two grams of dextran (Pharmacia Co.; average molecular weight $\overline{M}w$ 10,000) was dissolved in 18 ml of water. To the resulting solution was added 2 ml of 10% (M/V) sodium periodate. The mixture was incubated overnight at 4° C. with stirring. 5% sodium bisulfite was added dropwise to the reaction mixture until the brown color of iodine disappeared. Salts of low-molecular-weight compounds were removed by dialysis, and the resulting solution containing aldehyde-type activated dextran was lyophilized.

Fifteen milligrams of bilirubin oxidase having 1,4-diaminobutane bonded thereto, which was obtained in the same manner as in Example 2, was dissolved in 15 ml of 0.02M borate buffer (pH 10.0), and 450 mg of the aldehyde-type activated dextran obtained as above was added, and the mixture was incubated overnight at 4° C. The reaction mixture obtained was electrophoresed on sodium dodecylsulfate/polyacrylamide gels (gel concentration 10%; pH 8.9). No band of bilirubin oxidase was observed, and a broad continuous band was detected at a position corresponding to a molecular weight of about 70,000 to 200,000. The recovered yield of the resulting bilirubin oxidase derivative was 83.3% based on bilirubin oxidase having 1,4-diaminobutane bonded to it.

EXAMPLE 4

Production of a Bilirubin Oxidase Derivative by Chemical Modification of a Partial Half-Butyl Esterified Copolymer of Styrene and Maleic Anhydride (1) Synthesis of a Copolymer of Styrene and Maleic Anydride Maleic anhydride (383 g; 3.9 moles) was added to 3.7 liters of cumene, and the mixture was stirred under refluxing of cumene. To the solution was added drowpise a solution of 16.3 g (60 mmoles) of dicumyl peroxide and 203 g (1.95 mole) of styrene in 1.7 liters of cumene dropwise over the course of about 40 minutes. After the addition, the mixture was stirred for 1 hour under heat. The reaction mixture was left to stand overnight. The supernatant was removed, and then the viscous product adhering to the vessel was recovered by dissolving it in acetone. Acetone was evaporated from the resulting solution to give 353 g of a styrene/maleic anhydride copolymer (SMA for short).

(2) Fractionation of SMA

SMA (120.0 g) obtained as above wa dissolved in 3 liters of acetone, and 4.9 liters of n-hexane was added dropwise with stirring for about 1 hour. The whitely turbid mixture of acetone and n-hexane was transferred to another vessel, and 9.74 liters of n-hexane was added dropwise with stirring over about 1.5 hours. The jelly-like substance adhering to the vessel wall was recovered by dissolving it in acetone. Acetone was evaporated under reduced pressure from the recovered solution. The residue was dried in vacuo overnight at 70° to 80° C. There was obtained 49.2 g of a fractionated precipitate of SMA.

The SMA fractionated precipitate (40.0 g) was dissolved in 1 liter of acetone, and 3.8 kg of glass beads (average particle diameter 0.1 mm) surface-treated with a silane were added to the solution. Acetone was evaporated to adhere SMA to the surface of the glass beads.

A column system obtained by filling the glass beads having SMA adhering thereto and 1.4 liters of a mixture of acetone and n-hexane (volume ratio 24:76 at 25° C.) into a column having an inside diameter of 80 mm and a length of 80 cm was maintained at 25° C. A mixture (1.6 liters) of acetone and n-hexane in a volume ratio of 24:76 at 25° C., and 6.0 liters of a mixture of acetone and n-hexane in a volume ratio of 37:63 at 25° C. and then acetone were supplied to the upper part of column dropwise. The effluent eluted with the 37:63 mixture of acetone and n-hexane were collected, Low-boiling compounds were evaporated from the effluent and the residue was dried overnight in vacuo at 70° to 80° C. to obtain 31.8 g of the desired fractionated SMA. The weight average molecular weight ($\overline{M}w$) and number average molecular weight ($\overline{M}n$) of this fractionated SMA were measured by gel permeation chromatography (GPC for short; tetrahydrofuran eluent, polystyrene as a standard substance). It was found to have a $\overline{M}w$ of 1340 and a $\overline{M}n$ of 1220 ($\overline{M}w/\overline{M}n = 1.10$). When measured by a vapor pressure osmometer, its $\overline{M}n$ was 1210. The maleic anhydride content of the fractionated SMA measured by potentiotitmetry was 47.3 mole %.

(3) Partial Half-Butyl Esterification of the Fractionated SMA

SMA fractionated by the above method (10.0 g), 2.20 g of n-butanol, 0.10 g of anhydrous lithium acetate and 20 ml of dioxane was put in an about 30 ml ampoule equipped with a magnetic stirrer, and the ampoule was sealed up. With stirring, the contents of the ampoule were heated at 90° C. for 20 hours. A portion of the resulting reaction mixture was sampled, and the amount of the unreacted n-butanol in it was determined by gas chromatography using ethyl Cellosolve as an internal standard. The degree of the half-butyl esterification of the maleic anhydride rings in the copolymer was calculated from the conversion of the charged n-butanol, and found to be 62 %. The reaction mixture was diluted with 20 ml of dioxane, and the diluted solution was added dropwise to 400 ml of n-hexane and reprecipitation was carried out. The precipitate was recovered and dried overnight in vacuo at about 60° C. to give 11.5 g of the desired partially half-butyl esterified copolymer of styrene and maleic anhydride (Bu-SMA for short). The content of the remaining maleic anhydride rings in Bu SMA was determined on the basis of the absorption intensity at wave numbers 1780 cm$^{-1}$ and 700 cm$^{-1}$ of its infrared absorption spectrum (FT-IR, KBr disk method), and found to be 30.3 mole % (one molecule of Bu-SMA contained 1.8 maleic anhydride rings on an average). By GPC, it was found to have a $\overline{M}w$ of 1530 and a $\overline{M}n$ of 1440 ($\overline{M}w/\overline{M}n = 1.06$).

(4) Synthesis of a Bilirubin Oxidase Derivative

Fifty Milligrams of Bilirubin Oxidase (Sigma Co.; molecular weight 52,000) was dissolved in 1 ml of 0.1M aqueous sodium bicarbonate solution (pH 8.0) at 37° C. with stirring. After dissolving, 16 mg (5 mM; this means the final concentration of Bu-SMA in the reaction mixture; the same applies hereinafter) of Bu-SMA as a solid powder was gradually added to the solution, and the mixture was incubated at 37° C. for 1 hour. The reaction mixture was filtered. The filtrate was charged onto a column (3×40 cm) filled with Sephadex ® G-100 (Pharmacia Co.) to perform gel filtration. A 20 mM mixed solution of ammonium bicarbonate and ammonium carbonate was used as an eluent, and the effluent was detected at 280 nm. The eluate in the absorption portion was separated and concentrated by an ultrafiltration membrane (Sartorius SM145-39) and lyophilized to give 40 mg of a white powder. The recovered yield of the bilirubin oxidase derivative was 90%.

It was determined that the resulting white powder was a bilirubin oxidase derivative in which 3 to 4 molecules on an average of Bu-SMA the mole ratio of was 1:1; the degree of butylesterification 60%; $\overline{M}w = 1600$) were bonded per molecule of bilirubin oxidase (bonding as a result of the reaction of the amino groups of bilirubin oxidase with the maleic anhydride rings of Bu-SMA).

TEST EXAMPLE 1

Half-Life in Blood of a Bilirubin Oxidase Derivative

A bilirubinoxidase derivative prepared in accordance with Example 1 and the same bilirubinoxidase as used in Example 1 were labelled with $^{125}I$, and each intravenously administered to rats (body weight about 200 g) in a dose of 500,000 cpm/rat. The concentration of these in blood were examined periodically by measuring the radioactivity in blood. The results are plotted in semilogarithum, and shown in FIG. 3. In the figure, the closed circles show the result of measurement on the on the bilirubin oxidase derivative, and the open circles, the result of measurement on bilirubin oxidase. From these results, it was confirmed that the half-lives in blood of bilirubin oxidase and the bilirubin oxidase derivative were 2.5 minutes and 190 minutes respectively The bilirubin oxidase derivative prepared in accordance with Example 4 was labelled with $^{125}I$ and its half-life in blood was also determined. This bilirubin oxidase derivative had a half-life of 83 minutes in blood.

TEST EXAMPLE 2

Reduction of the Bilirubin Level in Blood by the Bilirubin Oxidase Derivative

Figure 4:
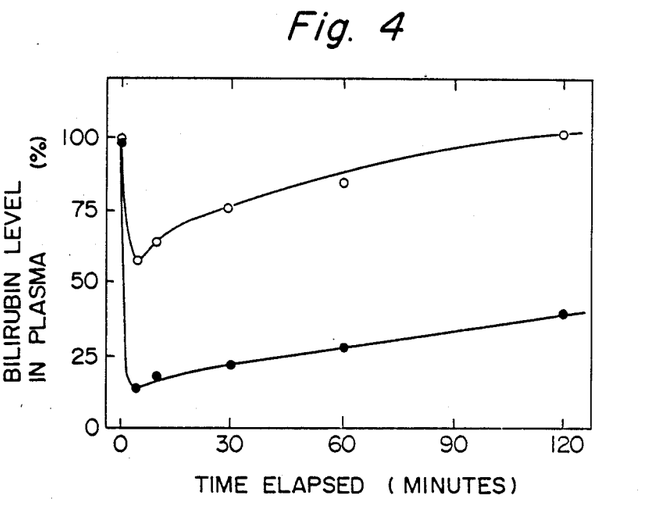
FIG. 4 is a graphic representation showing the concentrations of the bilirubin oxidase derivative obtained in Example 1 and bilirubin oxidase in the plasma which were measured with time in Test Example 2 with regard to jaundice model rats.

SD-strain rats (male, body weight about 200 g), 3 per group, were used. The abdomen of the rats was incised under ether anesthesia, and after bile duct ligation was carried out, the abdomen was closed. Bilirubin oxidase (5 mg/rat) or the bilirubin oxidase derivative obtained in Example 1 (5 mg/rat as bilirubin oxidase) was intravenously administered to jaundice model rats three days after the operation. Blood was drawn from the tail vein periodically. The blood was centrifuged (15,000 rpm, 12 seconds) to obtain a supernatant. Bilirubin in the plasma was measured. The results are shown in FIG. 4. In the figure, the closed circles show the results of measurement on the groups to which the bilirubin oxidase derivative was administered, and the open circles, the results of measurement on the groups to which bilirubin oxidase was administered.

TEST EXAMPLE 3

Figure 5:
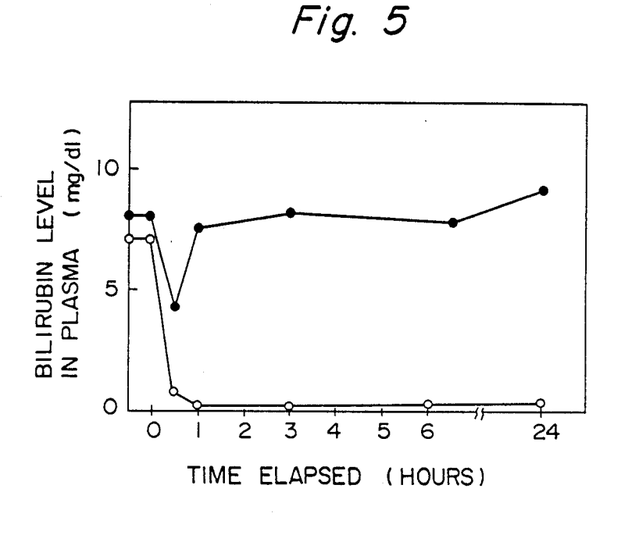
FIG. 5 is a graphic representation showing the concentrations of the bilirubin oxidase derivative obtained in Example 2 and bilirubin oxidase in the plasma which were measured with time in Test Example 3 with regard to jaundice model rats.

Reduction of the Bilirubin Level in Blood by the Bilirubin Oxidase Derivative Wistar-strain rats (male, body weight about 170 g), 4 per group, were used. The abdomen of the rats was incised under ether anesthesia, and after bile duct ligation was carried out, the abdomen was closed. Bilirubin oxidase (0.5 mg/rat) or the bilirubin oxidase derivative obtained in Example 2 (0.5 mg/rat as bilirubin oxidase) was intravenously administered to jaundice model rats three days after the operation. Blood was drawn from the heat or the tail vein periodically. The blood was centrifuged (3,000 rpm, 5 minutes) to obtain a supernatant. Bilirubin in the plasma was measured. The results are shown in FIG. 5. In the figure, the open circles show the results of measurement on the groups to which the bilirubin oxidase derivative was administered, and the closed circles, the results of measurement on the groups to which bilirubin oxidase was administered.

The results obtained in Test Examples 2 and 3 demonstrate that the bilirubin oxidase derivatives obtained by chemical modification with polyethylene glycol markedly reduce the bilirubin concentration in blood in jaundice model rats, and can maintain this condition for an extended period of time; and on the other hand, the bilirubin level reducing effect of bilirubin oxidase is only to a slight degree and rapidly disappears.

TEST EXAMPLE 4

Test for Antigenicity on a Bilirubin Oxidase Derivative

Rabbits were sensitized by subcutaneous injection (five administrations at two week intervals) of bilirubin oxidase and a bilirubin oxidase derivative obtained by chemical modification with polyethylene glycol. Blood was drawn from the animals, and centrifuged to obtain antibodies. Nine hundred microliters of each of bilirubin oxidase (0.35 unit) and the bilirubin oxidase derivative (0.35 unit as bilirubin oxidase) was added to 100 microliters of each of the antibodies, and the mixture was incubated at 37° C. for 15 minutes. The decrease of the enzyme activity was examined. The results are shown in Table 1.

TABLE I

Percent Inhibition of Box Activity by Antiserum Against Intact Box or Peg-Box(*)

| Antiserum raised in rabbit | Percent inhibition of enzyme activity | |
|---|---|---|
| | Native BOX | PEG-BOX |
| Anti-native BOX | 82.2 | 0 |
| Anti-PEG-BOX | 82.2 | 3.7 |

(*)BOX = bilirubin oxidase PEG-BOX = polyethylene glycol-modified bilirubin oxidase Table 1 shows that both of the antibodies inhibited the activity of non-modified bilirubin oxidase, but the activity of the modified bilirubin oxidase was not inhibited by any of the antibodies. This fact shows that by chemically modifying bilirubin oxidase, its antigenicity was lost.

FORMULATION EXAMPLE 1

Injectable solution:

| Ingredients | |
|---|---|
| (i) Polyethylene glycol-modified bilirubin oxidase | 100 mg |
| (ii) Physiological saline | 10 ml |

Method (1) Dissolve the active ingredient in physiological saline.
(2) Aseptically filter the solution obtained in step (1).
(3) Aseptically fill the sterilized solution into sterilized ampoules.
(4) Seal the ampoules under aseptic conditions.

FORMULATION EXAMPLE 2

Injectable Solution:

| Ingredients | |
|---|---|
| (i) Dextran-modified bilirubin oxidase | 100 mg |
| (ii) Physiological saline | 10 ml |

Method

Same as the method of Formulation Example 1 consisting of steps (1) to (4).

FORMULATION EXAMPLE 3

Injectable Solution:

| Ingredients | |
|---|---|
| (i) SMA-modified bilirubin oxidase | 100 mg |
| (ii) Physiological saline | 10 ml |

Method

Same as the method of Formulation Example 1 consisting of steps (1) to (4).

FORMULATION EXAMPLE 4

Drip:

| Ingredients | |
|---|---|
| (i) Polyethylene glycol-modified bilirubin oxidase | 500 mg |
| (ii) Glucose solution for injection | 500 ml |

Method (1) Dissolve the active ingredient in the glucose solution.
(2) Aseptically filter the solution obtained in step (1).
(3) Aseptically fill the sterilized solution in plastic containers for sterilized transfusions.
(4) Aseptically seal the plastic containers under aseptic conditions.

FORMULATION EXAMPLE 5

Drip:

| Ingredient | |
|---|---|
| (i) Dextran-modified bilirubin oxidase | 500 mg |
| (ii) Glucose solution for injection | 500 ml |

Method

Same as the method of Formulation Example 4 consisting of steps (1) to (4).

FORMULATION EXAMPLE 6

Drip:

| Ingredients | |
| --- | --- |
| (i) SMA-modified bilirubin oxidase | 500 mg |
| (ii) Glucose solution for injection | 500 ml |

Method

Same as the method of Formulation Example 4 consisting of steps (1) to (4).

ADVANTAGES OF THE INVENTION

The present invention provides bilirubin oxidase derivatives having the action of specifically decomposing and removing bilirubin in blood and a very long half-life in blood. The bilirubin oxidase derivatives are effective as drugs for treating jaundice.

We claim:

1. A bilirubin oxidase derivative resulting from covalent bonding of a water-soluble polymeric substance to bilirubin oxidase.

2. The bilirubin oxidase derivative of claim 1 in which the water-soluble polymeric substance is selected from the group consisting of polyalkylene glycols, polyvinyl alcohol, polysaccharides, a partially hydrolyzed or partially half-esterified copolymer of styrene and maleic anhydride, a partially hydrolyzed or partially half-esterified copolymer of divinyl ether and maleic anhydride, a partially hydrolyzed or partially half-esterified copolymer of acrylic acid and maleic anhydride, Ficoll, polyamino acids and albumin.

3. The bilirubin oxidase derivative of claim 1 in which the water-soluble polymeric substance is a polyalkylene glycol.

4. The bilirubin oxidase derivative of claim 1 in which the water-soluble polymeric substance is polyethylene glycol.

5. The bilirubin oxidase derivative of claim 1 in which the water-soluble polymeric substance is a polysaccharide.

6. The bilirubin oxidase derivative of claim 1 in which the water-soluble polymeric substance is dextran.

7. The bilirubin oxidase derivative of claim 1 in which the water-soluble polymeric substance is a partially hydrolyzed or partially half-esterified copolymer of styrene and maleic anhydride.

8. The bilirubin oxidase derivative of claim 1 in which the water-soluble polymeric substance is a partially half-butyl-esterified copolymer of styrene and maleic anhydride.

9. A pharmaceutical composition for treating jaundice comprising a therapeutically effective amount of at least one bilirubin oxidase derivative of claim 1 and a pharmaceutically acceptable adjuvant.

10. A method of treating jaundice which comprises administering an amount, effective for treating jaundice, of at least one bilirubin oxidase derivative of claim 1 to a patient with jaundice.

* * * * *